United States Patent
Tanaka et al.

(10) Patent No.: US 11,698,066 B2
(45) Date of Patent: Jul. 11, 2023

(54) PRESSURE-CONTROLLING DEVICE, AND PRESSURE-USING APPARATUS

(71) Applicant: Murata Manufacturing Co., Ltd., Kyoto (JP)

(72) Inventors: Nobuhira Tanaka, Kyoto (JP); Kenjiro Okaguchi, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 516 days.

(21) Appl. No.: 16/690,840

(22) Filed: Nov. 21, 2019

(65) Prior Publication Data
US 2020/0088213 A1  Mar. 19, 2020

Related U.S. Application Data

(63) Continuation of application No. PCT/JP2018/019458, filed on May 21, 2018.

(30) Foreign Application Priority Data

Jun. 1, 2017  (JP) ................................. 2017-108880

(51) Int. Cl.
*F04B 43/00*  (2006.01)
*A61M 1/00*  (2006.01)
(Continued)

(52) U.S. Cl.
CPC .............. *F04B 43/046* (2013.01); *A61M 1/74* (2021.05); *F04B 43/0081* (2013.01);
(Continued)

(58) Field of Classification Search
CPC .. F04B 43/046; F04B 43/0081; F04B 45/047; F04B 49/06; F04B 49/08; F04B 49/22;
(Continued)

(56) References Cited

U.S. PATENT DOCUMENTS 3,398,533 A * 8/1968 Wolfbauer, Jr. ........ F04B 35/06
  60/407
4,838,768 A   6/1989 Flaherty
(Continued)

FOREIGN PATENT DOCUMENTS

DE  102008034240 A1 * 1/2010 ......... B60G 17/0523
JP  H04-119373 U   10/1992
(Continued)

OTHER PUBLICATIONS

Machine Translation of DE-102008034240-A1 (obtained from USPTO Search, Copyright 2023 Clarivate Analytics) (Year: 2023).*
International Search Report for International Application No. PCT/JP2018/019458 dated Aug. 14, 2018.
Written Opinion for International Application No. PCT/JP2018/019458 dated Aug. 14, 2018.

*Primary Examiner* — Essama Omgba
*Assistant Examiner* — Geoffrey S Lee
(74) *Attorney, Agent, or Firm* — Pearne & Gordon LLP (57) ABSTRACT

A pressure-controlling device (10) includes a pump (21), a connection pipe (30), a first valve (41), and a second valve (42). The pump (21) has an inlet port (211) and an outlet port (212). The connection pipe (30) has a first end in communication with the outlet port (212), and a second end in communication with the inlet port (211) and that has a first space (31) that contains the first end, a second space (32) that contains the second end, and a third space (33) that is located between the first space (31) and the second space (32).

13 Claims, 5 Drawing Sheets

(51) Int. Cl.
*F04D 9/00* (2006.01)
*F04B 43/04* (2006.01)
*F04B 45/047* (2006.01)
*F04F 5/22* (2006.01)
*F04F 5/46* (2006.01)
*F04F 1/02* (2006.01)
*F04F 5/52* (2006.01)
*F04F 5/54* (2006.01)

(52) U.S. Cl.
CPC ............. *F04B 45/047* (2013.01); *A61M 1/82* (2021.05); *F04D 9/006* (2013.01); *F04F 1/02* (2013.01); *F04F 5/52* (2013.01)

(58) Field of Classification Search
CPC .... F04B 49/24; F04B 53/16; F04B 2205/063; F04B 2205/064; F04F 5/22; F04F 5/467; F04F 5/52; F04F 5/54; F04F 1/02; F04D 9/006; G05D 16/208; A61M 1/74; A61M 1/82; A61M 1/06; A61M 2210/0618; A61M 5/02225; A61M 5/0235; A61G 7/05769
See application file for complete search history.

(56) References Cited

U.S. PATENT DOCUMENTS

| | | | |
|---|---|---|---|
| 2005/0043677 | A1* | 2/2005 | Kelly .................... A61M 1/066 604/74 |
| 2010/0074775 | A1* | 3/2010 | Yamamoto ............ F04B 43/046 417/413.2 |
| 2014/0202424 | A1* | 7/2014 | Lou ........................... F01L 9/10 123/336 |
| 2015/0008795 | A1* | 1/2015 | Kang .................. H01L 41/1136 310/331 |
| 2015/0059749 | A1* | 3/2015 | Nitta .................. A61M 16/0003 128/204.18 |
| 2017/0173233 | A1* | 6/2017 | Tanaka ................ A61M 39/223 |

FOREIGN PATENT DOCUMENTS

| | | |
|---|---|---|
| JP | 2010-203349 A | 9/2010 |
| JP | 2013-213421 A | 10/2013 |
| WO | 2016/039083 A1 | 3/2016 |
| WO | WO-2016039083 A1 * | 3/2016 .......... A61M 1/0035 |

* cited by examiner

PRESSURE-CONTROLLING DEVICE, AND PRESSURE-USING APPARATUS

This is a continuation of International Application No. PCT/JP2018/019458 filed on May 21, 2018 which claims priority from Japanese Patent Application No. 2017-108880 filed on Jun. 1, 2017. The contents of these applications are incorporated herein by reference in their entireties.

BACKGROUND OF THE DISCLOSURE

Field of the Disclosure

The present disclosure relates to a pressure-controlling device that controls the pressure of a desired location, and a pressure-using apparatus that uses the pressure-controlling device.

Description of the Related Art

Various devices for controlling pressure by using fluid control of pumps have been contrived. For example, Patent Document 1 discloses a micro pump unit that includes micro pumps.

In the structure of the micro pump unit disclosed in Patent Document 1, the micro pumps are connected in serial. The micro pump unit disclosed in Patent Document 1 achieves a high pressure by combining separately controlled directions of flow paths of the micro pumps.

Patent Document 1: Japanese Unexamined Patent Application Publication No. 2010-203349

BRIEF SUMMARY OF THE DISCLOSURE

With the structure in Patent Document 1, however, the use of the connected micro pumps lead to a complex structure and an enlarged shape.

It is an object of the present disclosure to achieve a high pressure with a simple structure having a small size.

A pressure-controlling device according to the present disclosure includes a pump, a connection pipe, a first valve, and a second valve. The pump has an inlet port and an outlet port. The connection pipe has a first end in communication with the outlet port and a second end in communication with the inlet port and has a first space that contains the first end, a second space that contains the second end, and a third space that is located between the first space and the second space. The first valve switches between a state in which the first space and an exterior space of the connection pipe are in communication with each other and the first space and the third space are not in communication with each other, and a state in which the first space and the exterior space of the connection pipe are not in communication with each other and the first space and the third space are in communication with each other. The second valve switches between a state in which the second space and the third space are in communication with each other, and a state in which the second space and the third space are not in communication with each other.

With this structure, the discharge by the pump into the first space is carried out, and the states of the first valve and the second valve are switched. This enables the pressure of the second space to be lower than that in the case where the pump merely sucks from the second space.

A pressure-controlling device according to the present disclosure includes a pump, a connection pipe, a first valve, and a second valve. The pump has an inlet port and an outlet port. The connection pipe has a first end in communication with the inlet port and a second end in communication with the outlet port and has a first space that contains the first end, a second space that contains the second end, and a third space that is located between the first space and the second space. The first valve switches between a state in which the first space and an exterior space of the connection pipe are in communication with each other and the first space and the third space are not in communication with each other, and a state in which the first space and the exterior space of the connection pipe are not in communication with each other and the first space and the third space are in communication with each other. The second valve switches between a state in which the second space and the third space are in communication with each other, and a state in which the second space and the third space are not in communication with each other.

With this structure, the discharge by the pump into the second space is carried out, and the states of the first valve and the second valve are switched. This enables the pressure of the second space to be higher than that in the case where discharge by the pump into the second space is merely carried out.

In each pressure-controlling device according to the present disclosure, a wall that defines the second space of the connection pipe is preferably a movable wall that is movable in response to pressure.

With this structure, the behavior of the movable wall can be used for application that uses pressure.

Each pressure-controlling device according to the present disclosure preferably has the following structure. The pressure-controlling device includes a control unit that controls communication and non-communication caused by the first valve, and communication and non-communication caused by the second valve. The control unit switches between a first control aspect and a second control aspect to perform the aspect. In the first control aspect, the first valve maintains communication between the first space and the exterior space of the connection pipe and non-communication between the first space and the third space, and the second valve maintains communication between the second space and the third space. In the second control aspect, the first valve maintains non-communication between the first space and the exterior space of the connection pipe and communication between the first space and the third space, and the second valve maintains non-communication between the second space and the third space.

With this structure, the pressure of the second space is increased or decreased.

The pressure-controlling device according to the present disclosure preferably has the following structure.

The control unit also has a third control aspect in which the first valve maintains the communication between the first space and the exterior space of the connection pipe and the non-communication between the first space and the third space, and the second valve maintains the non-communication between the second space and the third space. The control unit performs the third control aspect between the first control aspect and the second control aspect.

With this structure, the pressure is inhibited from undesirably being increased or decreased due to the wrong timing of control for the first valve and the second valve during the transition from the first control aspect to the second control aspect.

The pressure-controlling device according to the present disclosure preferably has the following structure. The pressure-controlling device further includes a measurement unit that measures an operational state of a target for pressure control. The control unit controls an aspect of the first valve and an aspect of the second valve in accordance with a measured value that is outputted by the measurement unit.

With this structure, the pressure is controlled depending on the operational state of a target for pressure control.

A pressure-using apparatus according to the present disclosure includes a specific one of the above structures of the pressure-controlling device, a movable wall that defines the second space of the connection pipe and that is movable in response to pressure, and a suction elastic film to which the movable wall is connected.

With this structure, the pressure-using apparatus serves as, for example, a nasal aspirator or breast pump that uses negative pressure.

A pressure-using apparatus according to the present disclosure includes a specific one of the above structures of the pressure-controlling device, and a cuff or an air cell that uses the second space of the connection pipe.

With this structure, the pressure-using apparatus serves as, for example, a sphygmomanometer or a bedsore prevention mat that uses positive pressure.

According to the present disclosure, a high pressure is achieved with a simple structure having a small size.

DETAILED DESCRIPTION OF THE DISCLOSURE

Figure 1:
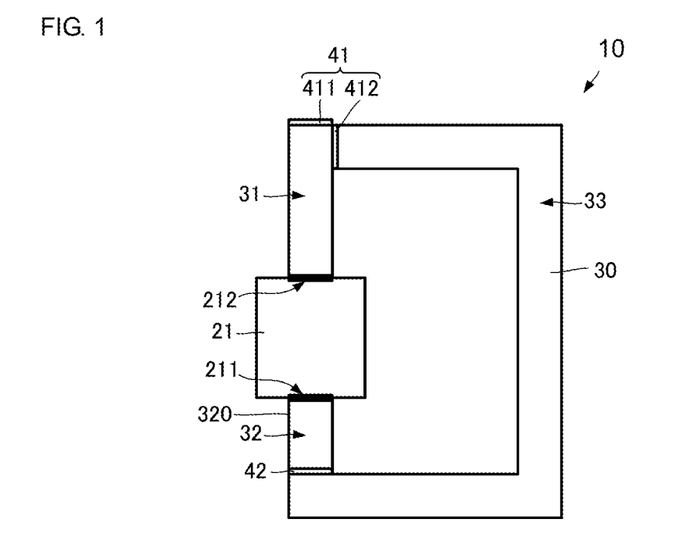
FIG. 1 illustrates the structure of a pump 21 and a connection pipe 30 of a pressure-controlling device 10 according to a first embodiment of the present disclosure.
Figure 2:
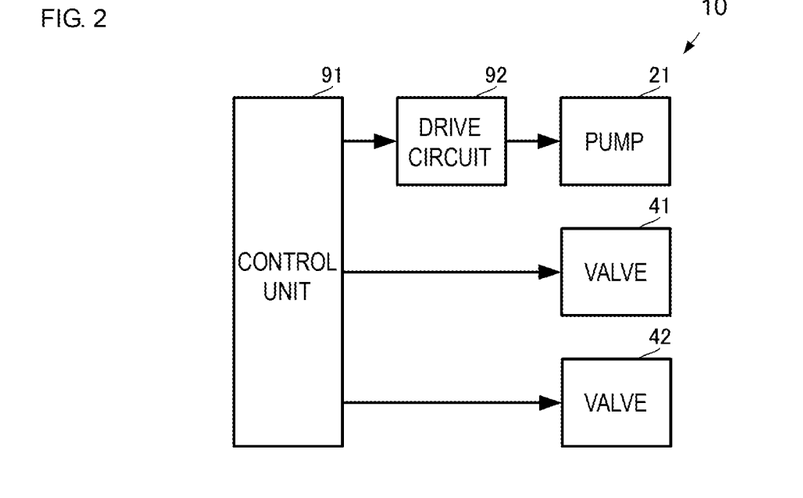
FIG. 2 is a functional block diagram of a control system of the pressure-controlling device 10 according to the first embodiment of the present disclosure.

A pressure-controlling device and a pressure-using apparatus according to a first embodiment of the present disclosure will be described with reference to the drawings. FIG. 1 illustrates the structure of a pump 21 and a connection pipe 30 of a pressure-controlling device 10 according to the first embodiment of the present disclosure. FIG. 2 is a functional block diagram of a control system of the pressure-controlling device 10 according to the first embodiment of the present disclosure.

As illustrated in FIG. 1 and FIG. 2, the pressure-controlling device 10 includes the pump 21, the connection pipe 30, a valve 411, a valve 412, a valve 42, a control unit 91, and a drive circuit 92. The valve 411 and the valve 412 are included in a valve 41. The valve 41 corresponds to a first valve according to the present disclosure. The valve 42 corresponds to a second valve according to the present disclosure.

As illustrated in FIG. 2, the control unit 91 outputs a drive control signal for the pump 21 to the drive circuit 92. The drive circuit 92 supplies a drive voltage to the pump 21 on the basis of the drive control signal. The pump 21 sucks and discharges fluid in response to the drive voltage. The control unit 91 controls the opening and closing of the valve 411, the valve 412, and the valve 42.

The opening and closing are controlled depending on a measured value that is outputted by a measurement unit (not illustrated). The measurement unit can measure one or more items of the pressure of the first space, the second space, or the third space, variation in the pressure during a predetermined time, the rate of the variation, and the ratio of the variation. In another embodiment, elapsed time after the pump starts operating, or elapsed time after a first control aspect, a second control aspect, or a third control aspect starts can be measured.

As illustrated in FIG. 1, the pump 21 has an inlet port 211 and an outlet port 212. The pump 21 includes, for example, a piezoelectric pump that uses the vibration of a piezoelectric element and a fluid control valve that restricts the direction of a flow path to one direction. The pump 21 sucks fluid (for example, gas) from the inlet port 211 and discharges the fluid (for example, the gas) from the outlet port 212.

The connection pipe 30 includes a pipe member. A first end of the connection pipe 30 is in communication with the outlet port 212. A second end of the connection pipe 30 is in communication with the inlet port 211. In the connection pipe 30, a first space 31, a third space 33, and a second space 32 are connected to each other in this order in the direction from the first end to the second end.

A wall of the first space 31 and a wall of the third space 33 of the connection pipe 30 are each composed of a rigid material. A wall 320 of the second space 32 of the connection pipe 30 is composed of an elastic body. That is, the wall 320 is a movable wall that vibrates in the direction perpendicular to a wall surface by the pressure of the second space 32. In this case, it is not necessary for the entire wall 320 to be composed of the elastic body, provided that at least a part of the wall 320 is composed of the elastic body. The elastic modulus of the wall 320 may be set, for example, such that during the operation described later, the second space 32 is not completely shrunk and the second space 32 has a predetermined hollow size.

The valve 411, the valve 412, and the valve 42 are, for example, solenoid valves. The control unit 91 controls the opening and closing of the solenoid valves, which are the valve 411, the valve 412, and the valve 42.

The valve 411 is disposed on the wall of the first space 31 of the connection pipe 30. When the valve 411 is closed, the first space 31 is isolated from the exterior space. When the valve 411 is opened, the first space 31 establishes the communication with the exterior space.

The valve 412 is disposed on the boundary between the first space 31 and the third space 33 of the connection pipe 30. In other words, the connection pipe 30 is divided into the first space 31 and the third space 33 by the valve 412. When the valve 412 is closed, the first space 31 and the third space 33 are isolated from each other. When the valve 412 is opened, the first space 31 and the third space 33 establish communication with each other.

The valve 42 is disposed on the boundary between the third space 33 and the second space 32 of the connection pipe 30. In other words, the connection pipe 30 is divided into the third space 33 and the second space 32 by the valve 42. When the valve 42 is closed, the third space 33 and the second space 32 are isolated from each other. When the valve 42 is opened, the third space 33 and the second space 32 establish communication with each other.

Figure 3A:
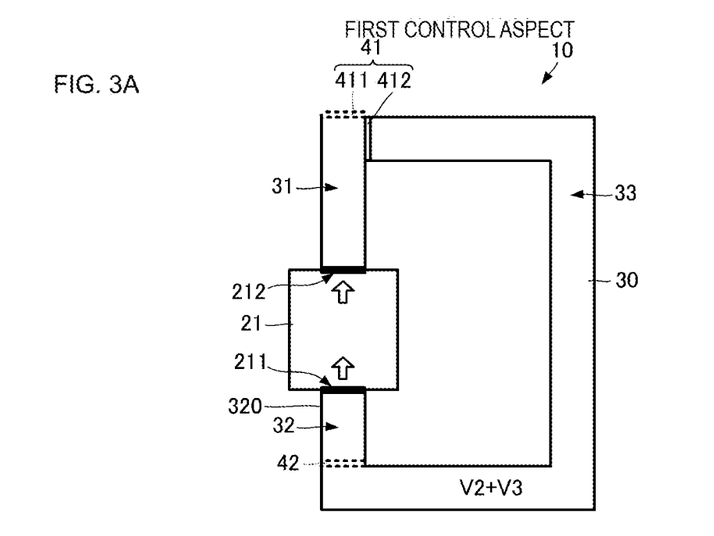
FIG. 3A illustrates a first control aspect of operation of the pressure-controlling device 10.
Figure 3B:
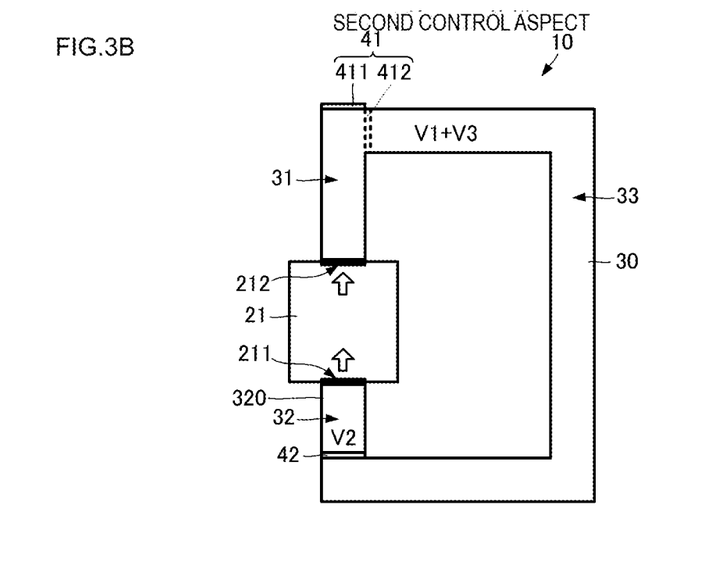
FIG. 3B illustrates a second control aspect of the operation of the pressure-controlling device 10.

With this structure, the pressure-controlling device 10 operates as follows. FIGS. 3A and 3B illustrate the operation of the pressure-controlling device 10 according to the first embodiment of the present disclosure. FIG. 3A illustrates the first control aspect of the operation of the pressure-controlling device 10. FIG. 3B illustrates the second control aspect of the operation of the pressure-controlling device 10.

The pressure-controlling device 10 operates according to the first control aspect illustrated in FIG. 3A and operates according to the second control aspect illustrated in FIG. 3B after a predetermined time.

(First Control Aspect)

The valve 411 is controlled to be opened. The valve 412 is controlled to be closed. The valve 42 is controlled to be opened. Consequently, the first space 31 is in communication with the exterior space and is not in communication with the third space 33 (non-communication). The second space 32 and the third space 33 are in communication with each other.

In this state, a closed space that is formed by the second space 32 and the third space 33 of the connection pipe 30 is in communication with the inlet port 211 of the pump 21. The outlet port 212 of the pump 21 is in communication with the exterior space with the first space 31 interposed therebetween.

When the pump 21 is driven in this state, the air in the closed space that is formed by the second space 32 and the third space 33 of the connection pipe 30 is sucked into the pump 21, and the sucked air is discharged to the exterior space. Consequently, the pressure of the closed space that is formed by the second space 32 and the third space 33 of the connection pipe 30 decreases to a pressure lower than the outside pressure, and this pressure is a negative pressure with respect to the outside pressure.

(Second Control Aspect)

The valve 411 is controlled to be closed. The valve 412 is controlled to be opened. The valve 42 is controlled to be closed. Consequently, the first space 31 and the third space 33 are in communication with each other. The second space 32 is isolated from the third space 33 (non-communication).

In this state, a closed space that is formed by the second space 32 of the connection pipe 30 is in communication with the inlet port 211 of the pump 21. A closed space that is formed by the first space 31 and the third space 33 of the connection pipe 30 is in communication with the outlet port 212 of the pump 21.

When the pump 21 is driven in this state following the first control aspect, the air in the closed space that is formed by the second space 32 of the connection pipe 30 is sucked into the pump 21, and the sucked air is discharged into the closed space that is formed by the first space 31 and the third space 33. Consequently, the pressure of the closed space that is formed by the second space 32 of the connection pipe 30 is a negative pressure lower than the pressure of the closed space that is formed by the first space 31 and the third space 33.

In the second control aspect, the pressure of the closed space that is formed by the first space 31 and the third space 33 of the connection pipe 30 is lower than the pressure of the first space 31 in the first control aspect.

Accordingly, the pressure of the second space 32 in the second control aspect is a negative pressure lower than the pressure of the second space 32 in the first control aspect. That is, the pressure of the second space 32 further decreases as compared with that in the first control aspect.

For example, the volume of the first space 31 is denoted by V1, the volume of the second space 32 is denoted by V2, the volume of the third space 33 is denoted by V3, the maximum static pressure of negative pressure at which the pump 21 can suck is denoted by P, and the pressure of the closed space that is formed by the second space 32 in the second control aspect is denoted by P2. According to Boyle's law, the pressure P2 can be calculated by using the following expression.

$$P2 = -P \times (1 + V3/Vall),$$

where Vall is the volume of a closed space that is formed by the first space 31, the second space 32, and the third space 33.

With this structure, the pressure of the second space 32 can be lower than the maximum static pressure of negative pressure at which the pump 21 can suck (the absolute value is larger than that). For example, the volume V1 of the first space 31 and the volume V2 of the second space 32 are decreased as much as possible, and the volume V3 of the third space 33 is increased as much as possible. This enables the pressure of the second space 32 to be about −40 kPa for the pump 21 the maximum static pressure of which is 20 kPa. That is, the absolute value of the pressure of the second space 32 is substantially twice.

Also, this structure, in which the single pump 21 suffices, is small and simple, and enables the absolute value of the pressure of the space to be high.

Figure 4:
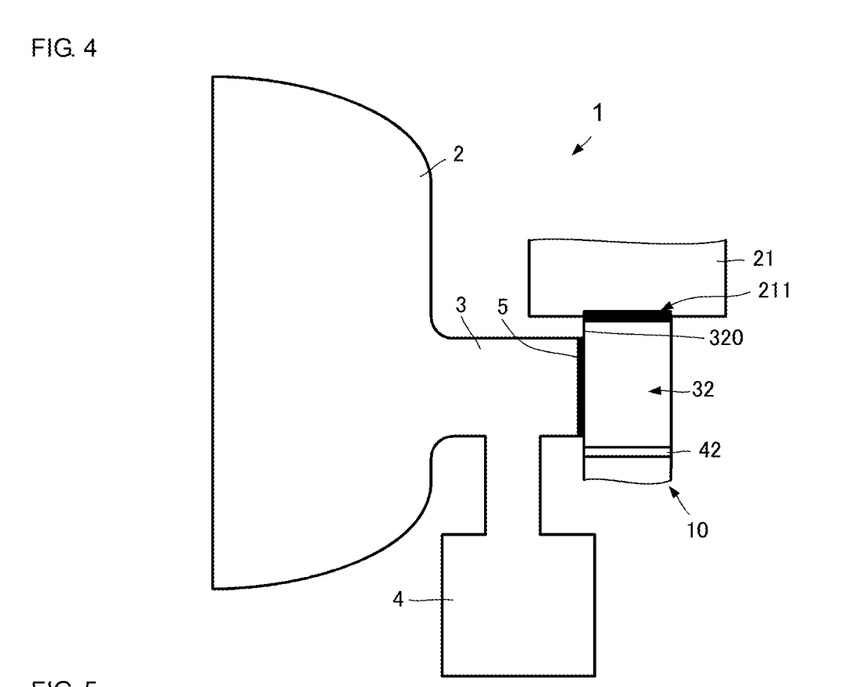
FIG. 4 schematically illustrates a sectional side view of the structure of a breast pump that is an example of a pressure-using apparatus 1 according to the first embodiment of the present disclosure.

The pressure-controlling device 10 can be used for the pressure-using apparatus 1 described below. FIG. 4 schematically illustrates a sectional side view of the structure of a breast pump that is an example of the pressure-using apparatus 1 according to the first embodiment of the present disclosure.

As illustrated in FIG. 4, the pressure-using apparatus 1 includes the pressure-controlling device 10 described above, a pad 2, a connection pipe portion 3, a liquid reservoir 4, and an elastic film 5. Here, the pressure-using apparatus 1 is a breast pump. The pad 2 has a cup shape and is to be attached to the breast. The connection pipe portion 3 is connected to the root of the cup shape of the pad 2. The liquid reservoir 4 that is tubular and the pad 2 are in communication with the connection pipe portion 3. A part of a wall of the connection pipe portion 3 is opened, and the elastic film 5 is fitted into a cavity thereof. The elastic film 5 is in contact with the wall 320 that defines the second space 32 of the pressure-controlling device 10. The elastic film 5 may form a part of the wall 320. The elastic film 5 corresponds to a suction elastic film according to the present disclosure.

With this structure, when the pressure-controlling device 10 is actuated, the wall 320 bends so as to extend toward the second space 32 due to a high negative pressure, and the elastic film 5 is pulled into the second space 32. This enables milking at the high negative pressure and improves the efficiency of milking more than an existing one.

According to the present embodiment, the pressure-using apparatus 1 is a breast pump. However, the use of the structure of the pressure-controlling device 10 according to the present disclosure improves the suction ability of an apparatus that sucks liquid such as a nasal aspirator.

Figure 5:
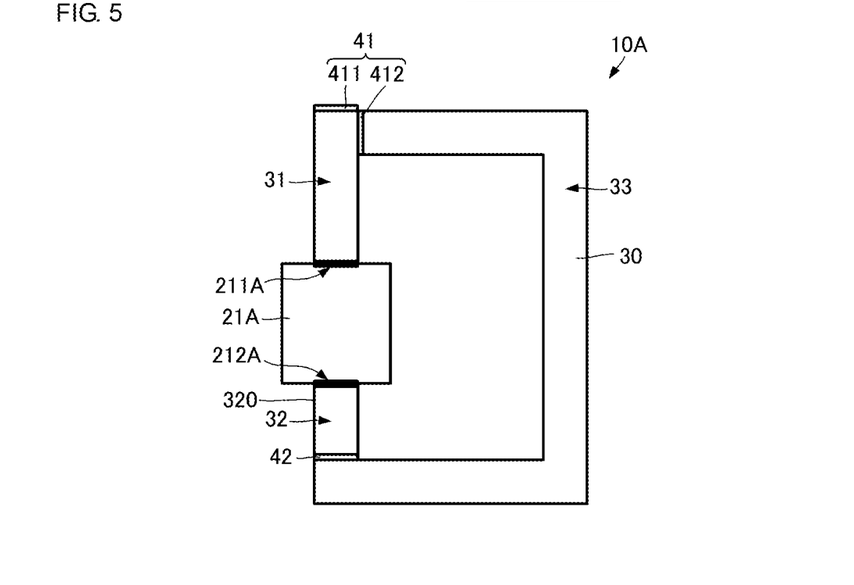
FIG. 5 illustrates the structure of a pump 21A and the connection pipe 30 of a pressure-controlling device 10A according to a second embodiment of the present disclosure.

A pressure-controlling device according to a second embodiment of the present disclosure will now be described with reference to the drawings. FIG. 5 illustrates the structure of a pump 21A and the connection pipe 30 of a pressure-controlling device 10A according to the second embodiment of the present disclosure.

The pressure-controlling device 10A according to the present embodiment differs from the pressure-controlling device 10 according to the first embodiment in that the pump 21 is replaced with the pump 21A. The other components of the pressure-controlling device 10A are the same as those in the pressure-controlling device 10, and a description of the same components is omitted.

The pump 21A has an inlet port 211A and an outlet port 212A as in the pump 21. The pump 21A includes, for example, a piezoelectric pump that uses the vibration of a piezoelectric element and a fluid control valve that restricts the direction of a flow path to one direction.

The inlet port 211A is in communication with the first end of the connection pipe 30, that is, an end portion of the connection pipe 30 near the first space 31. The outlet port 212A is in communication with the second end of the connection pipe 30, that is, an end portion of the connection pipe 30 near the second space 32.

Figure 6A:
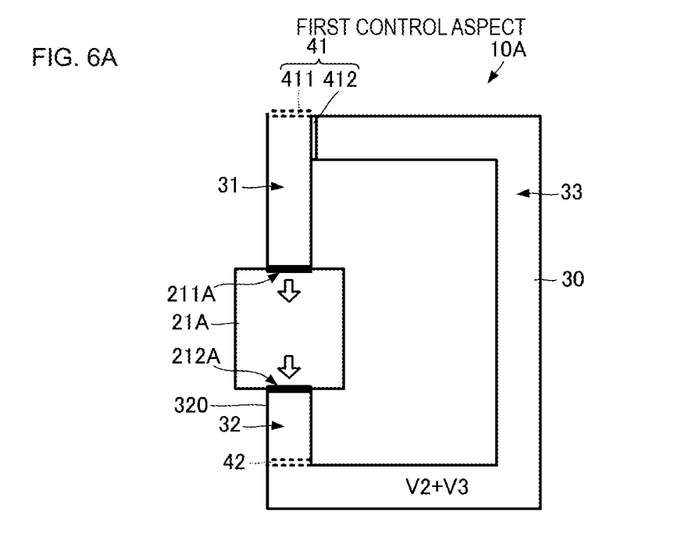
FIG. 6A illustrates a first control aspect of operation of the pressure-controlling device 10A.
Figure 6B:
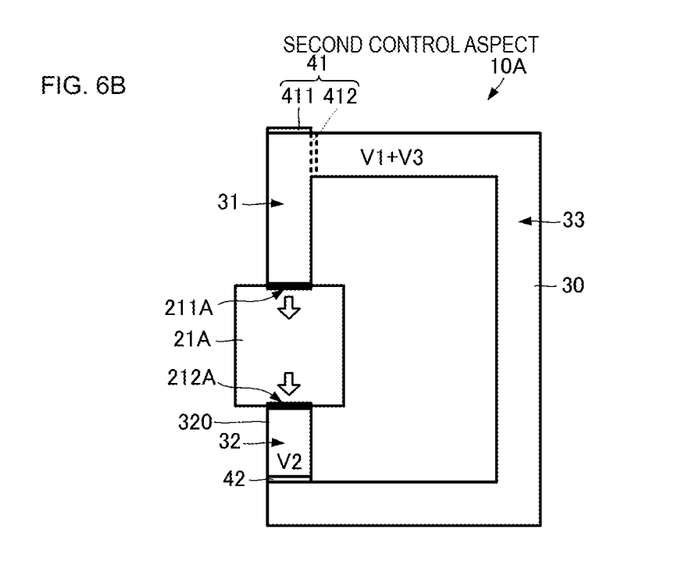
FIG. 6B illustrates a second control aspect of the operation of the pressure-controlling device 10A.

With this structure, the pressure-controlling device 10A operates as follows. FIGS. 6A and 6B illustrate the operation of the pressure-controlling device 10A according to the second embodiment of the present disclosure. FIG. 6A illustrates the first control aspect of the operation of the pressure-controlling device 10A. FIG. 6B illustrates the second control aspect of the operation of the pressure-controlling device 10A.

The pressure-controlling device 10A operates according to the first control aspect illustrated in FIG. 6A and operates according to the second control aspect illustrated in FIG. 6B after a predetermined time.

(First Control Aspect)

The valve 411 is controlled to be opened. The valve 412 is controlled to be closed. The valve 42 is controlled to be opened. Consequently, the first space 31 is in communication with the exterior space and is not in communication with the third space 33. The second space 32 and the third space 33 are in communication with each other.

In this state, the closed space that is formed by the second space 32 and the third space 33 of the connection pipe 30 is in communication with the outlet port 212A of the pump 21A. The inlet port 211A of the pump 21A is in communication with the exterior space with the first space 31 interposed therebetween.

When the pump 21A is driven in this state, air is sucked into the pump 21A from the exterior space, and the sucked air is discharged into the closed space that is formed by the second space 32 and the third space 33 of the connection pipe 30. Consequently, the pressure of the closed space that is formed by the second space 32 and the third space 33 of the connection pipe 30 increases to a pressure higher than the outside pressure, and this pressure is a high positive pressure with respect to the outside pressure.

(Second Control Aspect)

The valve 411 is controlled to be closed. The valve 412 is controlled to be opened. The valve 42 is controlled to be closed. Consequently, the first space 31 and the third space 33 are in communication with each other. The second space 32 is isolated from the third space 33.

In this state, the closed space that is formed by the first space 31 and the third space 33 of the connection pipe 30 is in communication with the inlet port 211A of the pump 21A. The closed space that is formed by the second space 32 of the connection pipe 30 is in communication with the outlet port 212A of the pump 21A.

When the pump 21A is driven in this state following the first control aspect, the air in the closed space that is formed by the first space 31 and the third space 33 of the connection pipe 30 is sucked into the pump 21A, and the sucked air is discharged into the closed space that is formed by the second space 32. Consequently, the pressure of the closed space that is formed by the second space 32 of the connection pipe 30 is higher than the pressure of the closed space that is formed by the first space 31 and the third space 33.

The pressure of the closed space that is formed by the first space 31 and the third space 33 of the connection pipe 30 in the second control aspect is higher than the pressure of the first space 31 in the first control aspect.

Accordingly, the pressure of the second space 32 in the second control aspect is a positive pressure higher than the pressure of the second space 32 in the first control aspect. That is, the pressure of the second space 32 increases.

With this structure, the pressure of the second space 32 can be higher than the maximum static pressure of the positive pressure that is available in the pump 21A. For example, the volume V1 of the first space 31 and the volume V2 of the second space 32 are decreased as much as possible, and the volume V3 of the third space 33 is increased as much as possible. This enables the pressure of the second space 32 to be about +40 kPa for the pump 21A the maximum static pressure of which is 20 kPa. That is, the absolute value of the pressure of the second space 32 is substantially twice.

Also, this structure, in which the single pump 21A suffices, is small and simple, and enables the absolute value of the pressure of the space to be high.

Figure 7:
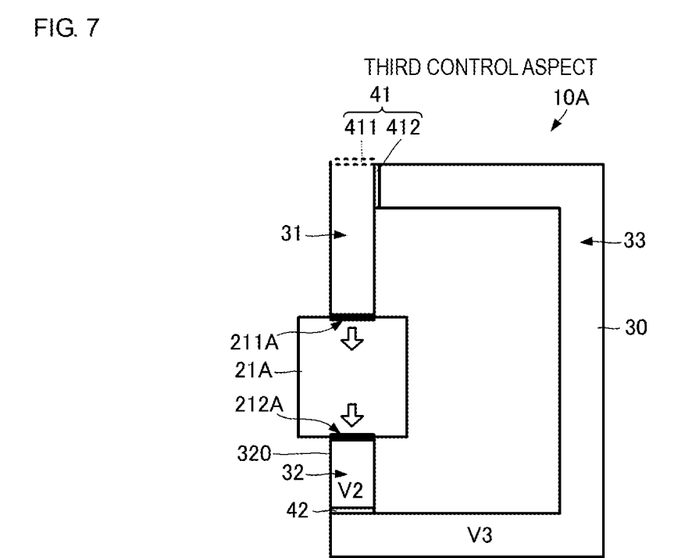
FIG. 7 illustrates a third control aspect of the operation of the pressure-controlling device 10A.

The pressure-controlling device 10A may perform a third control aspect described below during the transition from the first control aspect to the second control aspect. FIG. 7 illustrates the third control aspect of the operation of the pressure-controlling device 10A.

(Third Control Aspect)

The valve 411 and the valve 412 maintain the first control aspect. That is, the valve 411 is controlled to be opened. The valve 412 is controlled to be closed. The valve 42 is controlled to be closed. Consequently, the second space 32 is isolated from the third space 33.

With this structure, the second space 32 is isolated from the third space 33 before the first space 31 and the third space 33 are in communication with each other. For this reason, the pressure of the second space 32 can be inhibited from decreasing temporally as a result that the third space 33 establishes the communication with the first space 31 before the second space 32 is isolated from the third space 33, that is, the second space 32, the third space 33, and the first space 31 establish communication with each other.

The pressure-controlling device 10A can be used for, for example, a pressure-using apparatus such as a sphygmomanometer or a bedsore prevention mat. In this case, a cuff or an air cell is used for the second space 32 of the connection pipe 30. The second space 32 of the connection pipe 30 may be in communication with the cuff or the air cell. The meaning of the "cuff or the air cell that uses the second space of the connection pipe" according to the present disclosure includes an aspect in which the second space 32 itself is used as the cuff or the air cell and an aspect in which a space in communication with the second space 32 is used as the cuff or the air cell.

The third control aspect can be used for the pressure-controlling device 10 according to the first embodiment. In this case, the pressure of the second space 32 can be inhibited from increasing temporally.

Figure 8:
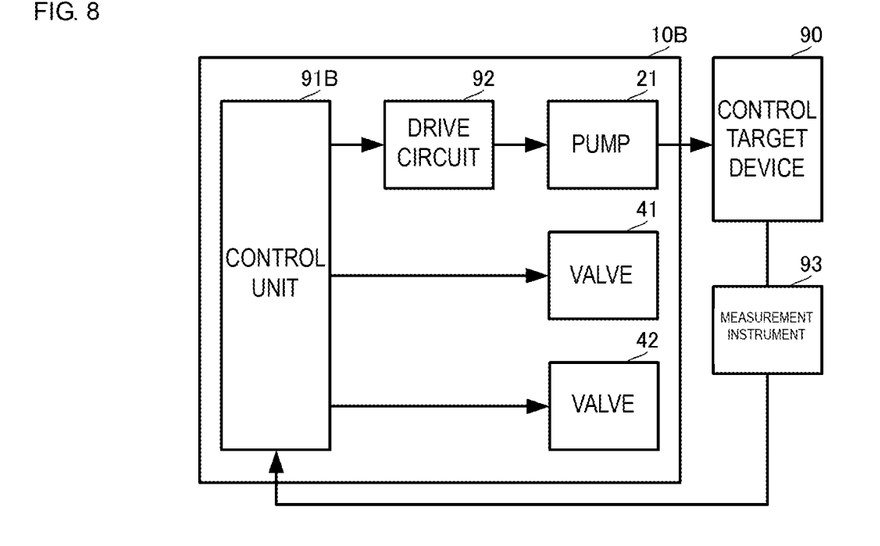
FIG. 8 is a functional block diagram of control systems of a system and a pressure-controlling device 10B having a feedback function.

According to the above embodiments, the absolute value of the pressure that is applied is merely increased. However, a structure described below enables the pressure that is applied to be appropriately adjusted. FIG. 8 is a functional block diagram of control systems of a system and a pressure-controlling device 10B having a feedback function.

The pressure-controlling device 10B includes a control unit 91B, the drive circuit 92, the pump 21, the valve 41, and the valve 42. The drive circuit 92, the pump 21, the valve 41, and the valve 42 have the same structure as those in the pressure-controlling device 10 or the pressure-controlling device 10A.

The system for providing the feedback function includes the pressure-controlling device 10B, a control target device 90, and a measurement instrument 93. The control target device 90 corresponds to a portion other than the pressure-controlling device 10B of the pressure-using apparatus such as a sphygmomanometer or a nasal aspirator. The measurement instrument 93 obtains a predetermined measured value of the control target device 90. For example, the measurement instrument 93 obtains a Korotkov sound as the measured value when serving as a sphygmomanometer and obtains the flow rate as the measured value when serving as a nasal aspirator. The measurement instrument 93 outputs the measured value to the control unit 91B.

The control unit 91B refers to the measured value and selects the pressure control for increasing the absolute value of the above pressure or normal pressure control to implement the control. For example, when rapid suction or increase in the pressure is necessary, the pressure control for increasing the absolute value of the above pressure is implemented, and when not necessary, the normal pressure control is implemented.

With this structure, the pressure control can be implemented in accordance with circumstances of the operation of the control target device 90.

1: pressure-using apparatus
2: pad
3: connection pipe portion
4: liquid reservoir
5: elastic film
10, 10A, 10B: pressure-controlling device
21, 21A: pump
30: connection pipe
31: first space
32: second space
33: third space
41: first valve
42: second valve
90: control target device
91, 91B: control unit
92: drive circuit
93: measurement instrument
211: inlet port
211A: inlet port
212: outlet port
212A: outlet port
320: wall
411: valve
412: valve

The invention claimed is:

1. A pressure-controlling device comprising:
a pump having an inlet port and an outlet port;
a connection pipe having a first end, a second end, a first space, a second space and a third space, wherein the first end is in communication with the outlet port, the second end is in communication with the inlet port, the first space contains the first end, the second space contains the second end, and the third space is located between the first space and the second space;
a first valve configured to switch between a state in which the first space and an exterior space of the connection pipe are in communication with each other and the first space and the third space are not in communication with each other, and a state in which the first space and the exterior space of the connection pipe are not in communication with each other and the first space and the third space are in communication with each other; and
a second valve configured to switch between a state in which the second space and the third space are in communication with each other, and a state in which the second space and the third space are not in communication with each other,
wherein the pressure-controlling device is adapted to operate in a first control aspect in which the first valve maintains communication between the first space and the exterior space of the connection pipe and non-communication between the first space and the third space, and the second valve maintains communication between the second space and the third space.

2. The pressure-controlling device according to claim 1, wherein a wall defining the second space of the connection pipe is a movable wall movable in response to pressure.

3. The pressure-controlling device according to claim 1, further comprising:
a control unit configured to control communication and non-communication caused by the first valve, and communication and non-communication caused by the second valve,
wherein the control unit is configured to switch between the first control aspect, and
a second control aspect in which the first valve maintains non-communication between the first space and the exterior space of the connection pipe and communication between the first space and the third space, and the second valve maintains non-communication between the second space and the third space.

4. The pressure-controlling device according to claim 3, wherein, in a third control aspect, the first valve maintains the communication between the first space and the exterior space of the connection pipe and the non-communication between the first space and the third space, and the second valve maintains the non-communication between the second space and the third space, and
wherein the control unit is configured to perform the third control aspect between the first control aspect and the second control aspect.

5. The pressure-controlling device according to claim 4, further comprising:
a measurement unit configured to measure an operational state of a target for pressure control,
wherein the control unit is configured to control an aspect of the first valve and an aspect of the second valve in accordance with a measured value outputted by the measurement unit.

6. The pressure-controlling device according to claim 3, further comprising:
a measurement unit configured to measure an operational state of a target for pressure control,
wherein the control unit is configured to control an aspect of the first valve and an aspect of the second valve in accordance with a measured value outputted by the measurement unit.

7. A pressure-using apparatus comprising:
a structure of the pressure-controlling device according to claim 1;
a movable wall defining the second space of the connection pipe and movable in response to pressure; and
a suction elastic film to which the movable wall is connected.

8. The pressure-controlling device according to claim 1, wherein the first valve comprises a valve configured to allow the first space and the exterior space to communicate, and wherein the first valve comprises another valve configured to allow the first space and the third space to communicate.

9. A pressure-controlling device comprising:
a pump having an inlet port and an outlet port;
a connection pipe having a first end, a second end, a first space, a second space and a third space, wherein the first end is in communication with the inlet port, the second end is in communication with the outlet port, the first space contains the first end, the second space contains the second end, and the third space is located between the first space and the second space;
a first valve configured to switch between a state in which the first space and an exterior space of the connection pipe are in communication with each other and the first space and the third space are not in communication with each other, and a state in which the first space and the exterior space of the connection pipe are not in communication with each other and the first space and the third space are in communication with each other; and a second valve configured to switch between a state in which the second space and the third space are in communication with each other, and a state in which the second space and the third space are not in communication with each other,
wherein the pressure-controlling device is adapted to operate in a first control aspect in which the first valve maintains communication between the first space and the exterior space of the connection pipe and non-communication between the first space and the third space, and the second valve maintains communication between the second space and the third space.

10. A pressure-using apparatus comprising:
a structure of the pressure-controlling device according to claim 9; and
a cuff or an air cell using the second space of the connection pipe.

11. The pressure-controlling device according to claim 9, wherein a wall defining the second space of the connection pipe is a movable wall movable in response to pressure.

12. The pressure-controlling device according to claim 9, further comprising:
a control unit configured to control communication and non-communication caused by the first valve, and communication and non-communication caused by the second valve,
wherein the control unit is configured to switch between the first control aspect and
a second control aspect in which the first valve maintains non-communication between the first space and the exterior space of the connection pipe and communication between the first space and the third space, and the second valve maintains non-communication between the second space and the third space.

13. The pressure-controlling device according to claim 9, wherein the first valve comprises a valve configured to allow the first space and the exterior space to communicate, and wherein the first valve comprises another valve configured to allow the first space and the third space to communicate.

* * * * *